United States Patent [19]

Sosnowski et al.

[11] Patent Number: 5,250,025
[45] Date of Patent: Oct. 5, 1993

[54] PERCUTANEOUS ACCESS CATHETER AND METHOD OF USE

[75] Inventors: Stephen A. Sosnowski, Oceanside; John H. Parrish, La Jolla; Alan J. Schempp, San Clemente, all of Calif.

[73] Assignee: Intramed Laboratories, San Diego, Calif.

[21] Appl. No.: 819,452

[22] Filed: Jan. 10, 1992

Related U.S. Application Data

[63] Continuation-in-part of Ser. No. 567,929, Aug. 15, 1990, abandoned.

[51] Int. Cl.$^5$ ............... A61M 31/00; A61M 29/00
[52] U.S. Cl. ............................... 604/51; 604/101
[58] Field of Search ..................... 604/96-103, 604/104, 107, 50-53; 606/192-194, 196

[56] References Cited

U.S. PATENT DOCUMENTS

| | | | |
|---|---|---|---|
| 4,284,081 | 8/1981 | Kasper et al. | 604/170 X |
| 4,571,239 | 2/1986 | Heyman | 624/54 |
| 4,636,199 | 1/1987 | Victor | 604/164 |
| 4,932,958 | 6/1990 | Reddy et al. | 606/192 |
| 4,950,257 | 8/1990 | Hibbs et al. | 604/265 |
| 4,969,875 | 11/1990 | Ichikawa | 604/164 |
| 4,978,341 | 12/1990 | Niederhauser | 604/167 |
| 5,007,898 | 4/1991 | Rosenbluth et al. | 604/54 |

OTHER PUBLICATIONS

Liguory, I. et al.: "Dilation Instrumentale et Cholangioscopie Transparieto-Hepatique pour Stenose d'Anastomose Choledocoduodenale avec Empierrement," L'Press Medicale, vol. 15 (10), pp. 481-483, 1986.

Trambert, Jonathan et al.: "Percutaneous Transhepatic Balloon Dilation of Benign Biliary Strictures," American Journal of Roentgenology, vol. 149, pp. 945-948 (1987).

Clayman, R. U. et al.: *Techniques in Endourology: A Guide to the Percutaneous Removal of Renal and Urethral Calculi*, ch. 5, pp. 113-120.

Dorfman, G. S. et al.: Investigative Radiology, vol. 23, pp. 441-446 (Jun. 1988).

Routh, W. et al.: "Tube Tamponade: Potential Pitfall in Angiography of Arterial Hemorrhage Associated with Percutaneous Drainage Catheters," Radiology, vol. 174, pp. 945-949.

*Primary Examiner*—John D. Yasko
*Assistant Examiner*—Adam J. Cermak
*Attorney, Agent, or Firm*—Freilich Hornbaker Rosen

[57] ABSTRACT

A percutaneous access catheter is employed for examining and treating internal body cavities and organs via an access tract. For example, the catheter can be employed for examining and treating the gallbladder via a transhepatic tract. The examination may employ endoscopic, fluoroscopic, ultrasonic, or other techniques; the treatment may employ surgical, chemical, or physical modalities. The catheter includes two inflation elements. These inflation elements control hemorrhaging and leakage of fluids from the internal body cavity or organ and reduce migration of the catheter within the internal body cavity or organ during the examination and/or treatment. The first inflation element is a toroidal elastic balloon located at the distal end of the device which serves to restrict the accidental or unintended removal of the distal end from the internal body cavity or organ. The second inflation device is an inflatable nondistensible sleeve which serves to anchor the device to the access tract during the medical procedure. The two inflation elements can act cooperatively so as to anchor the internal body cavity or organ to the access tract and so as to reduce the migration of the distal end of the device within the internal body cavity or organ. The inflation of the inflatable nondistensible sleeve can also serve to control hemorrhaging from the access tract by the application of tamponage without causing unwanted dilation thereof.

2 Claims, 3 Drawing Sheets

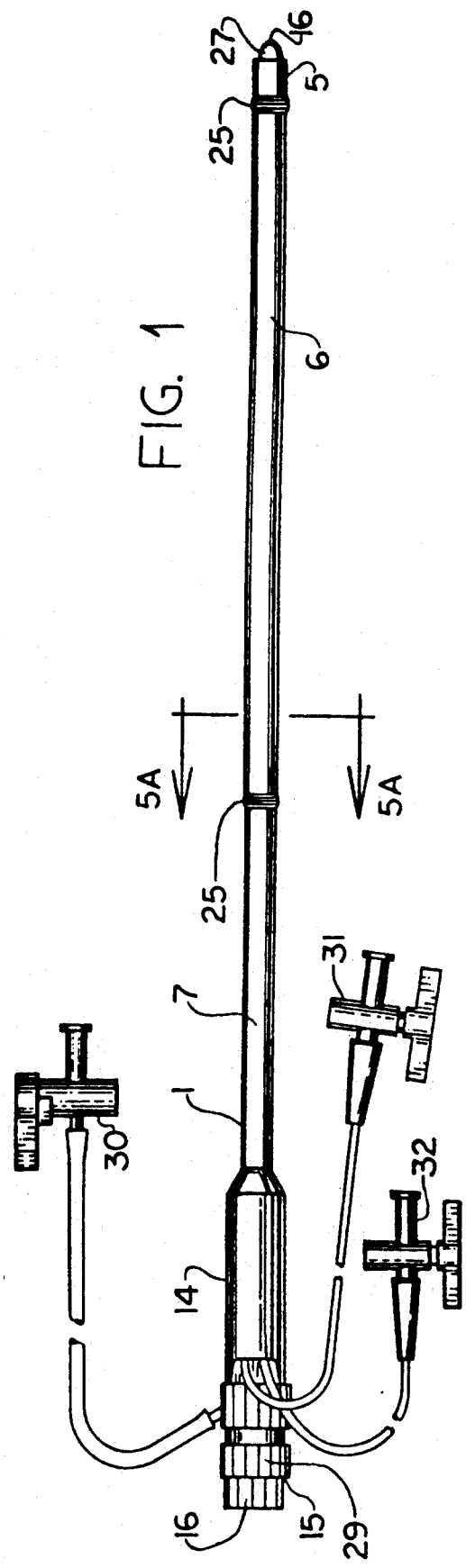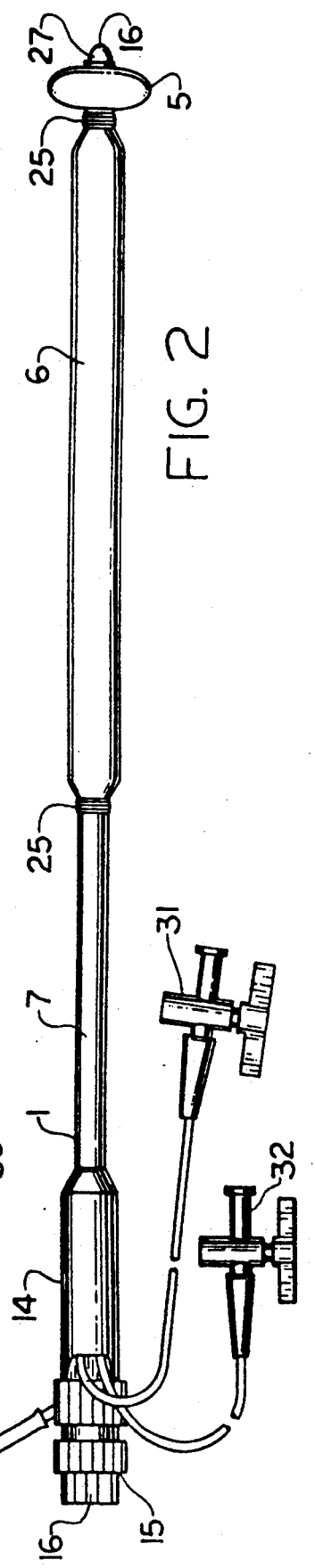

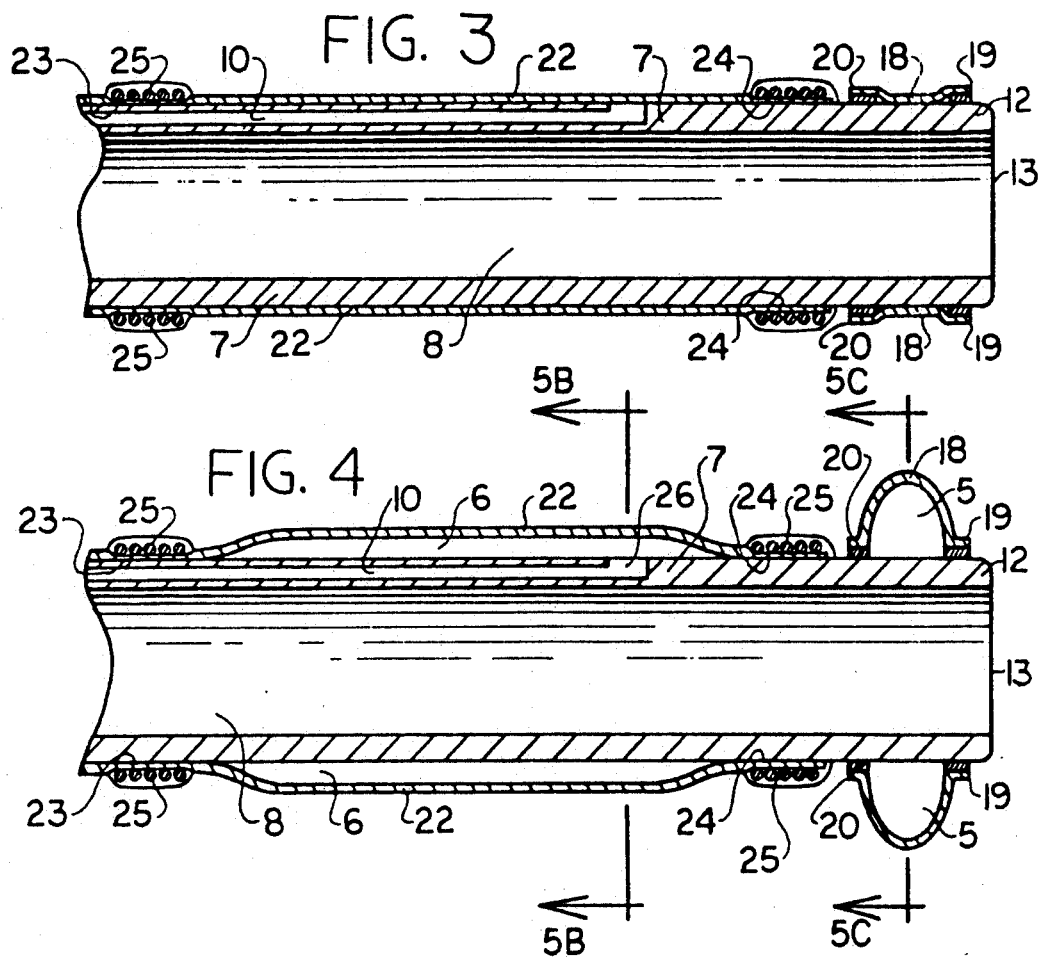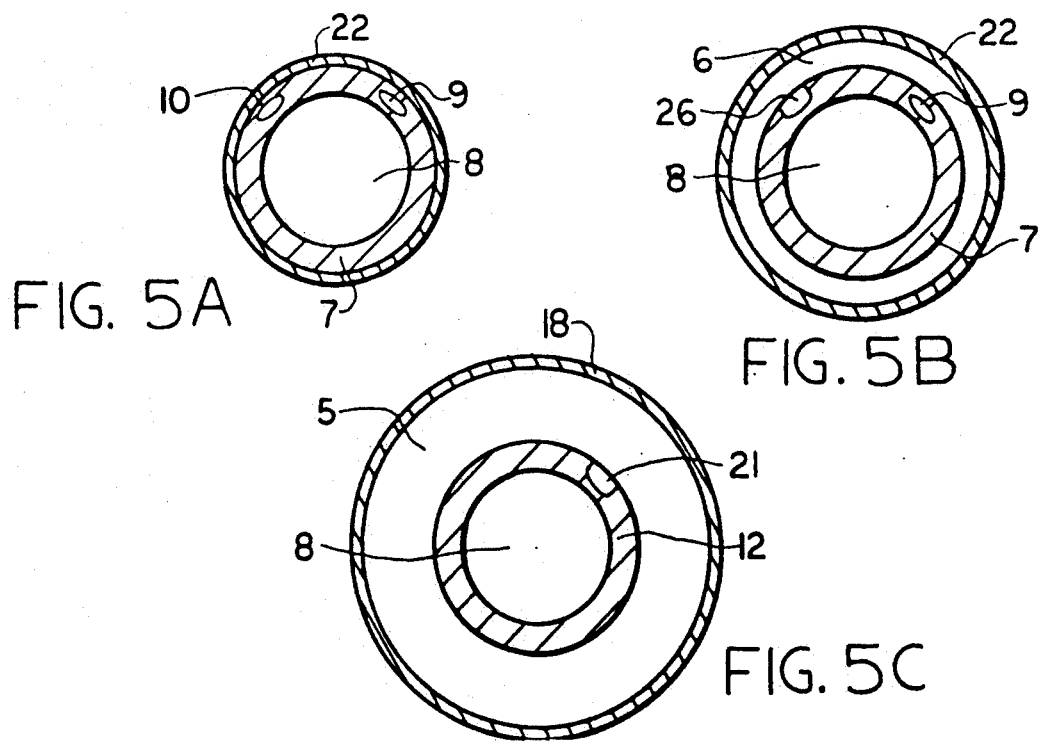

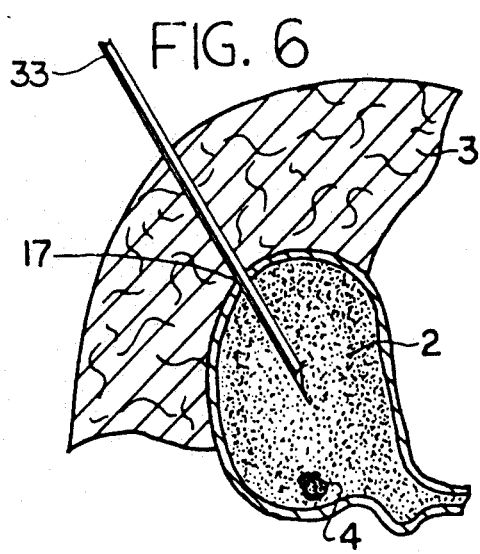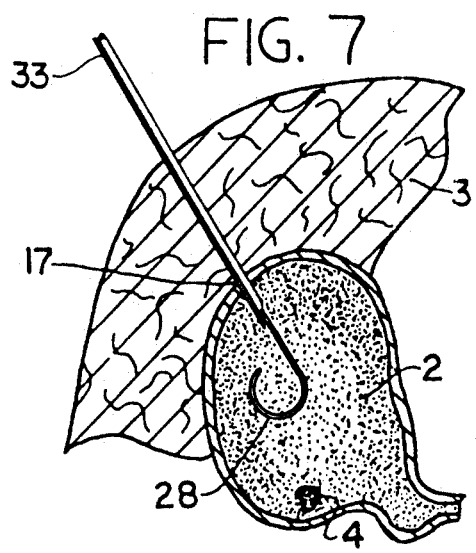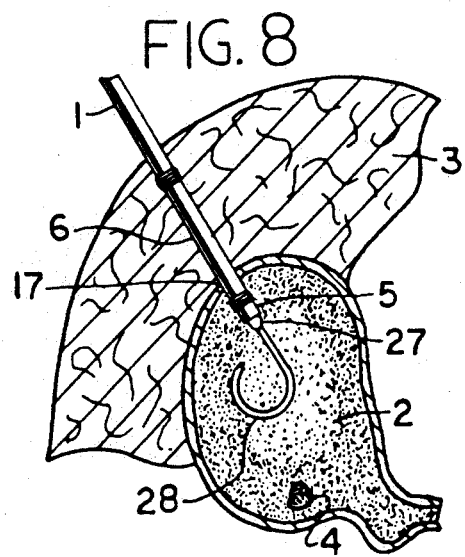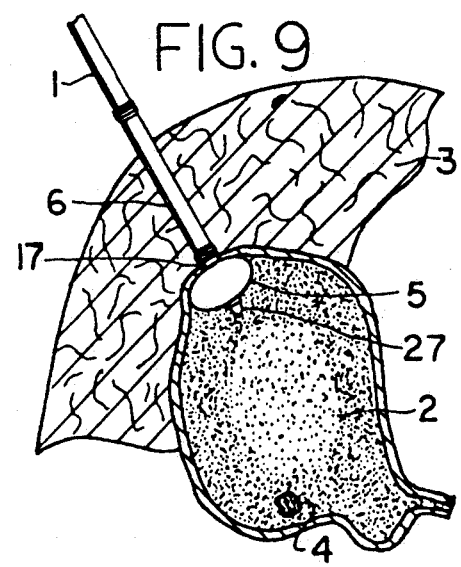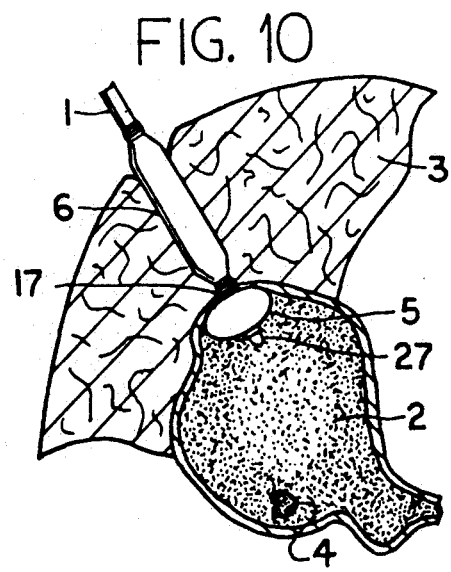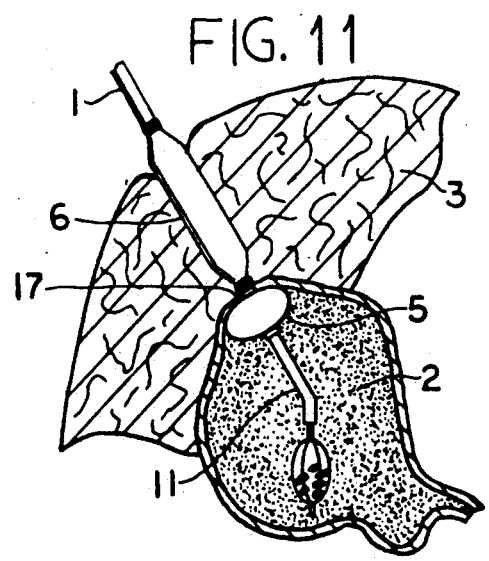

PERCUTANEOUS ACCESS CATHETER AND METHOD OF USE

This application is a continuation-in-part of 07/567,929 filed Aug. 15, 1990 now abandoned.

BACKGROUND

The invention relates to percutaneous access catheters for providing access to internal body cavities and organs via a surgically induced access tract. More particularly, the invention relates to percutaneous access catheters having inflation elements for securing the placement of the catheter within the access tract, for coupling the internal body cavity or organ to the access tract, for preventing migration of the catheter within the internal body cavity or organ, and for controlling hemorrhage from the access tract by the application of tamponage.

It is known to employ inflation elements in conjunction with percutaneous access catheters for performing a variety of functions. For example, a Foley type drainage catheter can be employed for draining bile fluids by percutaneously inserting the catheter into a transhepatic tract or channel leading to a cholecystostomic opening within the gallbladder or biliary tree. The distal end of the Foley catheter conventionally includes a toroidal inflatable balloon proximal to the drainage port. When the toroidal balloon is inflated, it becomes larger than the ostomic opening and, consequently, restricts the withdrawal of the port from the biliary tree. If the Foley balloon is pulled tightly against the ostomic opening, the balloon can also serve to occlude the ostomic opening so as to prevent or reduce the leakage of bile fluids from the biliary tree into the transhepatic tract. It is also known to employ inflation elements in conjunction with percutaneous dilation catheters of the type used for dilating strictures and/or stenoses. Such a dilation catheter can be employed to increase fluid flow within an internal body cavity or organ. For example, balloon catheters for dilating biliary strictures and stenoses are described by both Liguory et al. and by Trambert et al. Both Liguory and Trambert teach that balloon catheters may be percutaneously inserted into an ostomic opening within the biliary tree and positioned therein for dilating strictures and stenoses. [Liguory, I. et al.: "Dilation Intrumentale et Cholangioscopie Transpariento-hepatique pour Stenose d'Anastonose Choledoco-duodenale avec Empierrement." *L: Press Medicale* (1986), vol. 15 (10), pages 481–483; Trambert, Jonathan et al.: "Percutaneous Transhepatic Balloon Dilation of Benign Biliary Strictures," *American Journal of Roentgenology* (1987), vol. 149 pages 945–948].

It is also known to employ inflation elements in conjunction with percutaneous dilation catheters of the type used for enlarging the diameter of an access tract. Such a dilation catheter can be employed to prepare an access tract for insertion of a percutaneous access catheter. For example, one such dilation catheter is described by Rutner, i.e. the Cook Enforcer (TM) Balloon Catheter. [Rutner, A. B.: "Percutaneous Nephrolithotripsy through a Fresh Tract Facilitated by Working Through a Separate Cannula or Sheath," paper presented at the Western Section AUA, 1985.] Further examples of percutaneous dilation catheters are provided by Clayman et al and by Dorfman et al. [Clayman, Ralph V. and Castaneda Zuniga, Wilfrido: *Techniques in Endourology: A Guide to the Percutaneous Removal of Renal and Ureteral Calculi*, Chapter 5, "Dilation of the Nephrostomy Tract" pages 113–120 (Year Book Medical Publishers, Chicago & London - 1984); Dorfman, Gary S. Esparza, Alfredo R., and Cronan, John J.: *Investigative Radiology*, vol. 23, pages 441–446 (June 1988), "Percutaneous Large Bore Venotomy and Tract Creation: Comparison of Sequential Dilator and Angioplasty Balloon Methods in a Porcine Model—Preliminary Report."] A conventional protocol for the use of such a dilation catheter teaches that the initial access tract may be formed by means of a puncture with a needle or canula. The needle may include a guidewire within its lumen. When the needle is withdrawn from the access tract, the guidewire is left behind. A dilation catheter may then be inserted over the guidewire into the access tract. The balloon of the dilator may then be activated so as to enlarge the diameter of the access tract. If a relatively large access tract is desired, a series of dilators may be employed for increasing the diameter of the access tract step-wise. When inflated, the balloon of each dilator within the series dilates the tract to a size which then allows the next dilator to be inserted into the tract without significant tissue damage. Both Clayman and Dorfman indicate that, when a series of increasingly larger dilators is employed to dilate a percutaneous tract, the smallest incremental increase with respect to the size of each successive dilator within the series is 2 French. Accordingly, the difference in size between the fully inflated and fully deflated states of any of the balloons within the series of dilators must equal or exceed 2 French. Otherwise, clinically significant tissue damage could occur during a serial dilation procedure if, after dilating an access tract by less than 2 French, an attempt were then made to insert the next larger sized dilator into the tract.

And finally, it is also known to employ inflation elements in conjunction with percutaneous tamponade catheters. Routh et al. disclose that, if the insertion of a percutaneous drainage catheter causes acute hemorrhaging from an access tract, the hemorrhaging may be controlled by temporarily removing the percutaneous drainage catheter and inserting and activating an angioplasty balloon catheter. However, before the angioplasty balloon catheter is activated, it should be aligned with the arterial hemorrhage by angiography. Once hemorrhaging is controlled, the angioplasty balloon catheter may be deflated and removed and the percutaneous drainage catheter may be re-inserted. [Routh, William et al.: "Tube Tamponade: Potential Pitfall in Angiography of Arterial Hemorrhage Associated with Percutaneous Drainage Catheters," *Radiology*, vol. 174, pages 945–949.]

SUMMARY

The present invention is directed to an improved percutaneous access catheter and a method for using same. Embodiments of the invention are intended for examining and treating various internal body cavities and organs via various access tracts. For example, a preferred embodiment is employed for examining the gallbladder and for treating gallbladder disease. With respect to the examination of the gallbladder, this preferred embodiment provides percutaneous access through either the liver or the peritoneum into the gallbladder for facilitating endoscopic, fluoroscopic, ultrasonic, and/or other methods of examination. With respect to the treatment of gallbladder disease, this preferred embodiment provides similar access into the gallbladder for introducing forceps thereinto and for extracting stones therefrom. Embodiments of the invention can also facilitate other therapeutic modalities. For example, it can be used in conjunction with the fragmentation of larger stones by means of laser energy, electrohydraulic lithotriptor, or other mechanical means. The smaller fragments generated can then be extracted. Additionally, the catheter can be employed for introducing chemical reagents into the gallbladder for dissolving stones.

A percutaneous access catheter in accordance with the invention is designed to gain access to an internal body cavity or organ via an access tract. The access tract is a surgically induced pathway between the skin and the organ or cavity of interest. The access tract may traverse cutaneous tissue, subcutaneous fat, muscle tissue, fascia, parenchymal tissue, and/or other tissues which lie between the starting point and the target. The access tract may be of a type which is subject to hemorrhage and may terminate with an incision or ostomic opening within the cavity or organ of interest.

When the percutaneous access catheter is positioned in the access tract, it penetrates the ostomic opening. A port at the distal end of the catheter opens onto the internal body cavity or organ and provides access thereto via a hollow conduit which runs the length of the device.

A percutaneous access catheter in accordance with the invention employs various inflation elements to resolve various problems which are attendant to providing access to the internal body cavities and organs. The attendant problems resolved by the use of inflation elements include the following:

1. Hemorrhaging from the access tract.
2. Leakage of fluids such as bile from the internal body cavity or organ into the access tract.
3. Migration of the distal end of the catheter within the internal body cavity or organ due to the patient's breathing or other movements.

After a percutaneous access catheter in accordance with the invention is guided into the access tract and into the internal body cavity or organ under the guidance of medical imaging, a toroidal elastic balloon at the distal end of the device is inflated. The inflation of the toroidal elastic balloon serves to restrict the accidental or unintended withdrawal or removal of the distal end of the device from the internal body cavity or organ during the medical procedure.

A percutaneous access catheter in accordance with the invention employs an inflatable nondistensible sleeve for applying tamponage to the access tract and for anchoring the device to the access tract during the medical procedure. After the toroidal elastic balloon is inflated, the catheter is gently urged in an outward direction. The application of this retrograde force serves to urge the inflated toroidal elastic balloon against the ostomic opening of the internal body cavity or organ, which in turn causes the internal body cavity or organ to be drawn toward the access tract. While continuing to urge the catheter in this retrograde direction, the inflatable nondistensible sleeve is then inflated. In a preferred mode, upon inflation, the circumference of the nondistensible sleeve increases by only 1.3 French so as not to cause further dilation to any substantial extent.

The combined inflations of the toroidal elastic balloon and of the inflatable nondistensible sleeve have several effects. Firstly, the inflation of the inflatable nondistensible sleeve serves to apply tamponage to the access tract. If the access tract is hemorrhaging, such tamponage serves to control the bleeding. In the preferred mode, the tamponage is applied to the access tract without causing substantial dilation thereof.

Furthermore, combined inflations of the toroidal elastic balloon and of the inflatable nondistensible sleeve serve to enhance the positioning and steadiness of the catheter within the internal body cavity or organ. The toroidal elastic balloon and the inflatable nondistensible sleeve act synergistically so as to anchor the internal body cavity or organ to the access tract. Such anchoring serves to reduce migration of the catheter within the internal body cavity or organ. For example, an unanchored transhepatic catheter placed within the gallbladder can migrate within or from the gallbladder as the patient breaths. Such migration cay interfere with the surgical and other manipulative modalities performed via the catheter within the gallbladder. The combined inflations of the toroidal elastic balloon and of the inflatable nondistensible sleeve can serve to control such migrations.

Furthermore, combined inflations of the toroidal elastic balloon and of the inflatable nondistensible sleeve serve to occlude the ostomic opening so as to reduce the loss of fluids such as bile from the internal body cavity or organ. For example, a cholecystostomic opening into the gallbladder may allow bile to leak into the access tract. The leakage of bile into the liver can be pernicious. The occlusion of the cholecystostomic opening can serve to control the passage of bile from the gallbladder into the access tract.

BRIEF DESCRIPTION OF THE DRAWINGS

FIG. 1 is a perspective view of the percutaneous access catheter in accordance with a preferred embodiment of the invention illustrating the toroidal elastic balloon and the elongated sleeve in their deflated configurations.

FIG. 2 is a perspective view of the catheter of FIG. 1 illustrating the toroidal elastic balloon and the elongated sleeve in their inflated configurations.

FIG. 3 is a sectional view of a fragment of the catheter of FIG. 1 illustrating the toroidal elastic balloon and the elongated sleeve in their deflated configurations.

FIG. 4 is a sectional view of a fragment of the catheter of FIG. 2 illustrating the toroidal elastic balloon and the elongated sleeve in their inflated configurations.

FIGS. 5 (a)-(c) are sectional views of the catheter of FIG. 1 illustrating the hollow conduit and various inflation elements.

FIG. 5 (a) illustrates the first and second lumens for inflating and deflating the toroidal elastic balloon and the inflatable nondistensible sleeve and illustrates the inflatable nondistensible sleeve in its deflated configuration.

FIG. 5 (b) illustrates the first lumen for inflating and deflating the toroidal elastic balloon, illustrates the opening from the second lumen to the inflatable nondistensible sleeve for inflating and deflating same, and illustrates the inflatable nondistensible sleeve in its inflated configuration.

FIG. 5(c) illustrates the opening from the first lumen for inflating and deflating the toroidal elastic balloon and illustrates the toroidal elastic balloon in its inflated configuration.

FIGS. 6–11 illustrate the placement and use of the percutaneous access catheter with respect to the removal of gallstones from a gallbladder via a transhepatic route.

FIG. 6 illustrates the initial percutaneous puncture through the liver and into the gallbladder.

FIG. 7 illustrates the placement of a guidewire into the gallbladder.

FIG. 8 illustrate the placement of the catheter over the guidewire into the gallbladder.

FIG. 9 illustrates the inflation of the toroidal elastic balloon at the distal end of the catheter for restricting its displacement from the gallbladder.

FIG. 10 illustrates the inflation of the inflatable nondistensible sleeve at the distal end of the catheter for anchoring the device within its transhepatic tract and for controlling hemorrhaging therefrom.

FIG. 11 illustrates the insertion of forceps or other instrumentation through the catheter into the gallbladder and the use of such instrumentation for grasping a gallstone.

DETAILED DESCRIPTION

The percutaneous access catheter (1) in accordance with a preferred embodiment of the invention is a device for providing access to internal body cavities and organs, such as the biliary tree or gallbladder (2). The catheter (1) is particularly well adapted for providing access to internal body cavities and organs via a route which includes parenchymal tissue, such as the liver (3). In the preferred mode, the catheter (1) is employed for performing diagnostic and therapeutic procedures within the internal body cavity or organ, such as the removal of stones (4). The catheter (1) is particularly useful because its position within the internal body cavity or organ is secured by two cooperating mechanisms, viz. a toroidal elastic balloon (5) which restricts the movement of the device within the internal body cavity or organ and an inflatable nondistensible sleeve (6) which anchors the device with respect to the access tract. The inflatable nondistensible sleeve (6) also serves to control the hemorrhaging from the access tract.

EXAMPLE OF THE APPARATUS

The percutaneous access catheter (1) may be employed for providing transhepatic access to the gallbladder (2) for removing stones (4) therefrom. In a preferred embodiment for this application, the catheter (1) may be constructed from a hollow shaft (7) having a large conduit (8) and two smaller ancillary lumens (9 & 10). The hollow shaft (7) may have a rigid or flexible composition such as polyurethane, stainless steel, or materials of similar properties. The conduit (8) runs the entire length of the hollow shaft (7) and serves to pass operative endoscopes, forceps and other therapeutic instrumentation (11) into the biliary tree or gallbladder (2). The conduit (8) leads at the distal end (12) of the hollow shaft (7) to a distal port (13). At the proximal end (15) of the hollow shaft (7), the conduit (8) leads to a proximal port (15). In a preferred embodiment, the distal and proximal ports (13 and 15) are aligned with the conduit (8) and have a conformation capable of passing a trocar (16) therethrough. When the catheter (1) is positioned within the patient, the distal port (13) penetrates a cholecystostomic opening (17) into the biliary tree or gallbladder (2) and provides access thereto through the conduit (8) and the proximal port (15) to the outside.

In a preferred embodiment, the hollow shaft (7) has an outside diameter of 0.200 inch and the conduit (8) has an inside diameter of 0.150 inch. The ancillary lumens (9 and 10) need not run the entire length of the hollow shaft (7). The first ancillary lumen (9) serves to inflate and deflate the toroidal elastic balloon (5). The second ancillary lumen (10) serves to inflate and deflate the inflatable nondistensible sleeve (6). Hence the ancillary lumens (9 and 10) need only to extend to their respective inflation elements. Furthermore, the preferred ancillary lumens (9 and 10) have a relatively small inside diameter since they merely serve to transmit the inflation fluids or gasses to and from their respective inflation elements. In the preferred embodiment, the length of the hollow shaft (7) is adapted to the particular application. For transhepatically accessing a biliary tree or gallbladder (2), the preferred hollow shaft (7) has a length of approximately 8½ inches.

Attached to the hollow shaft (7) are two inflation elements, i.e. a toroidal elastic balloon (5) and an inflatable nondistensible sleeve (6). In the preferred embodiment, the size and location of these two inflation elements is adapted to the particular application.

The toroidal elastic balloon (5) encircles the distal port (13) of the hollow shaft (7). When the toroidal elastic balloon (5) is in its deflated state, it lies flat against the hollow shaft (7). The toroidal elastic balloon (5) is in a deflated state prior to the placement of the percutaneous access catheter (1) into the patient. Deflation of the toroidal elastic balloon (5) is necessary in order to allow the device to pass through a transhepatic tract or other access tract prepared specifically for the placement of the device. Deflation of the toroidal elastic balloon (5) also allows the distal port (13) of the device to penetrate a preformed cholecystostomic opening (17) into the gallbladder or biliary tree or some other ostomic opening into an internal body cavity or organ. After the catheter (1) is positioned within the patient, the toroidal elastic balloon (5) is inflated so as to restrict the withdrawal of the distal port (13) of the device from the biliary tree or gallbladder (2). When the toroidal elastic balloon (5) is inflated, it is symmetrical about the hollow shaft (7). The inflated diameter of the toroidal elastic balloon (5) may be greater than its axial width. After the toroidal elastic balloon (5) is inflated, the catheter (1) can be urged slightly outward so that the inflated toroidal elastic balloon (5) is drawn against the cholecystostomic opening (17) and pulls the gallbladder (2) and/or biliary tree tightly against the liver (3) so as to control the loss of bile fluids into the transhepatic tract.

The preferred toroidal elastic balloon (5) can be constructed by sliding a first cylindrical sleevelet (18) over the distal port (13) onto the hollow shaft (7). In a preferred embodiment, the first cylindrical sleevelet (18) is about ⅜ inch long and is positioned immediately proximate to the distal port (13). The uninflated inside diameter of the first cylindrical sleevelet (18) should be substantially the same as the outside diameter of the hollow shaft (7), i.e. the first cylindrical sleevelet (18) should fit snugly onto the hollow shaft (7). The preferred first cylindrical sleevelet (18) has a distensible composition such as latex or silicone. The ends (19 and 20) of the first cylindrical sleevelet (18) are bonded to the hollow shaft (7) by means of cyanoacrylate adhesive or similar bonding means so as to form the enclosure which comprises the balloon (5). The first cylindrical sleevelet (18) is located over an opening (21) to the first ancillary port for inflating and deflating the enclosure which forms the toroidal elastic balloon (5).

The second inflatable element, i.e. the inflatable nondistensible sleeve (6) also encircles the hollow shaft (7). However, the inflatable nondistensible sleeve (6) is located between the toroidal elastic balloon (5) and the proximal port (15). Like the toroidal elastic balloon (5), the inflatable nondistensible sleeve (6) is in a deflated state prior to the placement of the catheter (1) into the patient. Deflation of the inflatable nondistensible sleeve (6) facilitates the passage of the device through the transhepatic tract. After the catheter (1) is positioned within the patient, the inflatable nondistensible sleeve (6) is inflated so as to anchor the device to the access tract through the liver (3) or other tissue. Inflation of the inflatable nondistensible sleeve (6) can also serve to control hemorrhage from the access tract by the application of tamponage.

The preferred inflatable nondistensible sleeve (6) can be constructed by sliding a second cylindrical sleevelet (22) onto the hollow shaft (7). In a preferred embodiment for a percutaneous transhepatic access catheter (1), the inflatable nondistensible sleeve (6) is approximately 6.0 inches in length and one end (24) is positioned immediately adjacent to the toroidal elastic balloon (5). The second cylindrical sleevelet (22) can have a substantially nondistensible composition such as radiation cross linked polyethylene. The nondistensible sleeve (6) should have an uninflated inside diameter which is substantially identical to the outside diameter of the hollow shaft (7) so that the two elements fit snugly with one another. On the other hand, in a preferred embodiment having a hollow shaft (7) with an outside diameter of 0.200 inch, the nondistensible sleeve (6) has an inflatable outside diameter of approximately 16 Fr. The nondistensible composition of the sleeve (6) limits the expansion of the sleeve (6) so as to avoid any substantial dilation of the access tract.

In the preferred embodiment, the nondistensible sleeve (6) has a maximum inflated circumference and a minimum deflated circumference. The maximum inflated circumference is delimited by the nondistensible composition of the nondistensible sleeve (6). The minimum deflated circumference is delimited by the contact between the nondistensible sleeve and the hollow shaft (7). In one preferred mode, the difference between the maximum inflated circumference and the minimum deflated circumference may be as great as 1.5 French. In another preferred mode, the difference between the maximum inflated circumference and the minimum deflated circumference may be 1.0 French or less. However, in the preferred mode, the difference between the maximum inflated circumference and the minimum deflated circumference should be approximately 1.3 French. Within this range, when the nondistensible sleeve (6) is deflated and the hollow shaft (7) is inserted into the access tract, the subsequent inflation of the nondistensible sleeve (6) to its maximum inflated circumference provides tamponage of the access tract for controlling hemorrhage therefrom without causing substantial dilation thereof.

The ends (23 and 24) of the second cylindrical sleevelet (22) can then be bonded to the hollow shaft (7) by first heat shrinking the ends (23 and 24) of the polyethylene onto the hollow shaft (7). In the preferred embodiment, a thread (25) is then wrapped around the section that is heat shrunk to the hollow shaft (7) and a thin layer of epoxy (tm) is then placed over the windings (25) so as to anchor the second cylindrical sleevelet (22) to the hollow shaft (7). The second cylindrical sleevelet (22) is located over an opening (26) to the second ancillary lumen (10) for inflating and deflating the enclosure which forms the nondistensible sleeve (6).

In a preferred embodiment, the conduit (8) of the percutaneous access catheter (1) contains a removable trocar (16). The trocar (16) is inserted into the conduit (8) so as to extend or protrude from the distal port (13). In a preferred embodiment, the trocar (16) has a rounded or blunted tip (27) which extends or protrudes about 0.10 inch from the distal port (13). The protruding tip (27) of the trocar (16) interacts with the distal end (12) of the hollow shaft (7). The bullet shaped taper formed by the hollow shaft (7) and the trocar (16) facilitates the atraumatic insertion of the device into the access tract and into the ostomic opening (17). The trocar (16) lends strength to the device. The trocar (16) may also include a small diameter lumen for passing a guidewire (28) through the length of the trocar (16). The guidewire serves to guide the device through the access tract. The trocar (16) can be withdrawn from the conduit (8) after the device is positioned within the patient.

The preferred embodiment also includes a hemostatic valve (29). At the proximal end (14) of the device, a conventional hemostasis valve (29), drilled out to have an inside diameter of 0.168 inch, can be bonded with polyvinylchloride cement to the hollow shaft (7). The hemostasis valve (29) serves to form a seal with the trocar (16) so as to prevent the passage of fluid through the conduit (8), e.g. blood or bile. If the trocar (16) is removed from the conduit (8) and replaced with an endoscope or some other therapeutic instrumentation (11), the hemostasis valve (29) can also serve to form a seal with such inserts.

A preferred embodiment also includes a drainage or fluid exchange port (30). The fluid exchange port (30) is attached to the hollow shaft (7) so as to open onto the conduit (8). The fluid exchange port (30) can be positioned below the hemostasis valve (29) on the hollow shaft (7) so as to by-pass the hemostasis valve (29). If it is desired to transfer liquids to and from the internal body cavity or organ, the trocar (16) is withdrawn to a point above the connection between the fluid exchange port (30) and the conduit (8). Liquid is then transferred to or from the internal body cavity or organ via the fluid exchange port (30) by opening or closing a valve controlling access to the fluid exchange port (30).

A preferred percutaneous access catheter (1) also includes two side ports, i.e. a first side port (31) and a second side port (32). The first side port (31) is connected with the first ancillary lumen (9) and is employable for inflating and deflating the toroidal elastic balloon (5). The second side port (32) is connected with the second ancillary lumen (10) and is employable for inflating and deflating the inflatable nondistensible sleeve (6).

EXAMPLE OF THE METHOD

In the preferred mode, a percutaneous access catheter (1) in accordance with the present invention is employed for transhepatically accessing the gallbladder (2) for examining and/or removing gallstones (4) therefrom. A transhepatic tract to the gallbladder should be prepared to facilitate the placement of the device within the patient. The transhepatic tract should include a cholecystostomic opening (17) for enabling the catheter (1) to penetrate into the gallbladder (2).

A transhepatic tract can be formed as follows. A 22 gauge Chiba needle (33) is inserted transhepatically under fluoroscopic and/or sonographic means through the fossa of the gallbladder into the central lumen of the organ. A guidewire (28) is then passed through the lumen of the needle (33) into the gallbladder (2) and the needle (33) is then removed over the guidewire (28). A series of progressively larger dilators can then be passed over the guidewire (28) and employed for enlarging the tract. The tract is dilated until a 14 Fr. transhepatic tract has been created. A catheter (1), having a outside diameter of 0.20 inch, can then be introduced through the 14 Fr. transhepatic tract. The catheter (1) is passed over the guidewire (28) by threading the guidewire (28) through the lumen in the trocar (16).

A cholangiogram may be employed to determine or confirm the location of the distal tip (27) within the gallbladder. The cholangiogram may be employed to determine or confirm the location of the distal tip (27) with the gallbladder. The cholangiogram is obtained by passing Renographin TM or other fluoroscopic dyes into the gallbladder through the fluid exchange port (30). Once the gallbladder (2) is charged with Renographin TM, a cholangiogram can be taken to verify the correct position of the distal port (13) within the gallbladder.

After it is determined that the distal port (13) is correctly positioned within the gallbladder, the toroidal elastic balloon (5) is inflated by passing fluid through the first ancillary lumen (9). In an alternative method of the invention, the inflation of the toroidal elastic balloon (5) can be omitted. Once the toroidal elastic balloon (5) is inflated, the catheter (1) can be pulled snugly such that the toroidal elastic balloon (5) pulls the gallbladder (2) tightly up against the liver (3). With the gallbladder (2) being held tightly against the liver (3), the nondistensible sleeve (6) is then inflated by passing fluid through the second ancillary lumen (10). Inflation of the nondistensible sleeve (6) serves to anchor the catheter to the transhepatic tract. Inflation of the nondistensible sleeve (6) also serves to control hemorrhaging from the transhepatic tract.

The inflation of the toroidal elastic balloon (5) and the inflatable nondistensible sleeve (6) operate jointly to anchor the gallbladder (2) to the liver (3). As a consequence, movement or migration of the distal port (13) within the gallbladder (2) is markedly less affected by the patient's breathing. The enhanced stability of the distal port (13) enhances the stability of medical instrumentation (11) which passes through the distal port (13) and facilitates the physician's manipulation of such medical instrumentation (11).

After the percutaneous access catheter (1) has been placed and anchored into position, the trocar (16) can be removed from the conduit (8). At this time an operative endoscope or other therapeutic instrument can be passed through the conduit (8) of the catheter into the gallbladder (2) Using forceps (34), under direct visualization via an endoscope, stones (4) can be grasped and extracted through the conduit (8) of the catheter (1). Larger stones (4) can be broken up via laser energy, by an electrohydraulic lithotriptor, or by mechanical means. The smaller fragments generated can then be extracted. Additionally, chemical methods can be employed for dissolving the stones (4).

Upon completion of the procedure, the toroidal elastic balloon (5) and the inflatable nondistensible sleeve (6) are deflated via the first and second side ports (31 & 32) using a syringe. The percutaneous access catheter (1) may then be removed from the transhepatic tract. A biliary T-tube may be put into place over the guide (28) in the gallbladder (2).

What is claimed is:

1. A method for accessing an internal body cavity or organ, the method comprising the following steps:
   Step A: forming an access tract to the internal body cavity or organ and forming an ostomic opening into the internal body cavity or organ for accessing the internal body cavity or organ by means of a percutaneous access catheter; then
   Step B: passing the percutaneous access catheter through the access tract and penetrating the internal body cavity or organ through the ostomic opening such that a distal port of the percutaneous access catheter opens onto the internal body cavity or organ for providing access thereto; then
   Step C: inflating a toroidal elastic balloon encircling the distal port of the percutaneous access catheter for restricting the removal of the distal port form the ostomic opening of the internal body cavity or organ; and
   Step D: inflating an inflatable nondistensible sleeve encircling a hollow shaft of the percutaneous access catheter for simultaneously controlling hemorrhage from the access tract and anchoring the hollow shaft within the access tract.

2. A method for accessing an internal body cavity or organ, the method comprising the following steps:
   Step A: forming an access tract to the internal body cavity or organ and forming an ostomic opening into the internal body cavity or organ for accessing the internal body cavity or organ by means of a percutaneous access catheter; then
   Step B: passing the percutaneous access catheter through the access tract and penetrating the internal body cavity or organ through the ostomic opening such that a distal port of the percutaneous access catheter opens onto the internal body cavity or organ; then
   Step C: inflating an inflatable nondistensible sleeve encircling a hollow shaft of the percutaneous access catheter for simultaneously controlling hemorrhage from the access tract and anchoring the hollow shaft within the access tract, the inflatable nondistensible sleeve being inflated without substantially dilating the access tract.

* * * * *